(12) United States Patent
Gazayerli

(10) Patent No.: US 8,535,254 B2
(45) Date of Patent: Sep. 17, 2013

(54) LUMBAR TRACTION DEVICE

(76) Inventor: M. Mounir Gazayerli, Bloomfield Hills, MI (US)

( * ) Notice: Subject to any disclaimer, the term of this patent is extended or adjusted under 35 U.S.C. 154(b) by 183 days.

(21) Appl. No.: 12/944,234

(22) Filed: Nov. 11, 2010

(65) Prior Publication Data

US 2011/0112456 A1    May 12, 2011

Related U.S. Application Data

(60) Provisional application No. 61/260,649, filed on Nov. 12, 2009.

(51) Int. Cl.
*A61F 5/00* (2006.01)

(52) U.S. Cl.
USPC .................. 602/36; 602/32; 602/60

(58) Field of Classification Search
USPC ... 602/32–40; 601/23, 33–35; 482/121–131, 482/907, 140, 78–80, 82, 139; 2/79, 227
See application file for complete search history.

(56) References Cited

U.S. PATENT DOCUMENTS

| | | | |
|---|---|---|---|
| 1,969,165 A * | 8/1934 | Turner ........................ 482/129 |
| 3,134,379 A | 5/1964 | Nightingale | |
| 4,865,022 A * | 9/1989 | Gorsen ........................ 602/33 |
| 5,256,119 A * | 10/1993 | Tudor ........................ 482/74 |
| 5,716,307 A | 2/1998 | Vadher | |
| 5,868,694 A | 2/1999 | Marlow et al. | |
| 6,544,152 B2 * | 4/2003 | Rosati ........................ 482/126 |
| 7,104,935 B2 | 9/2006 | Matsuoka | |
| 7,189,192 B2 * | 3/2007 | Edgeton ........................ 482/10 |
| 7,887,499 B2 * | 2/2011 | Cogswell ........................ 602/36 |
| 2003/0195092 A1 | 10/2003 | Basting | |
| 2007/0028346 A1 | 2/2007 | Williams | |
| 2008/0154165 A1 | 6/2008 | Ashihara et al. | |

OTHER PUBLICATIONS

Office Action mailed Jul. 11, 2012, U.S. Appl. No. 13/345,312, filed Jan. 6, 2012.

\* cited by examiner

*Primary Examiner* — Patricia Bianco
*Assistant Examiner* — Ophelia A Hawthorne
(74) *Attorney, Agent, or Firm* — Harness, Dickey & Pierce, PLC

(57) ABSTRACT

A lumbar traction device is herein disclosed. The lumbar traction device includes a lumbar support member to be worn adjacent to a lumbar region of a user, at least one lower leg support to be worn adjacent to a lower leg of the user, and at least one connecting member connecting the lumbar support member and the at least one lower leg support, the at least one connecting member being substantially inelastic. When a load is applied to the at least one lower leg support, the load is transferred to the lumbar support member via the at least one connecting member. When the load is transferred to the lumbar support member, the lumbar support member forcibly presses against the lower lumbar area of user, thereby distracting the hip bone from the lower vertebrae.

11 Claims, 5 Drawing Sheets

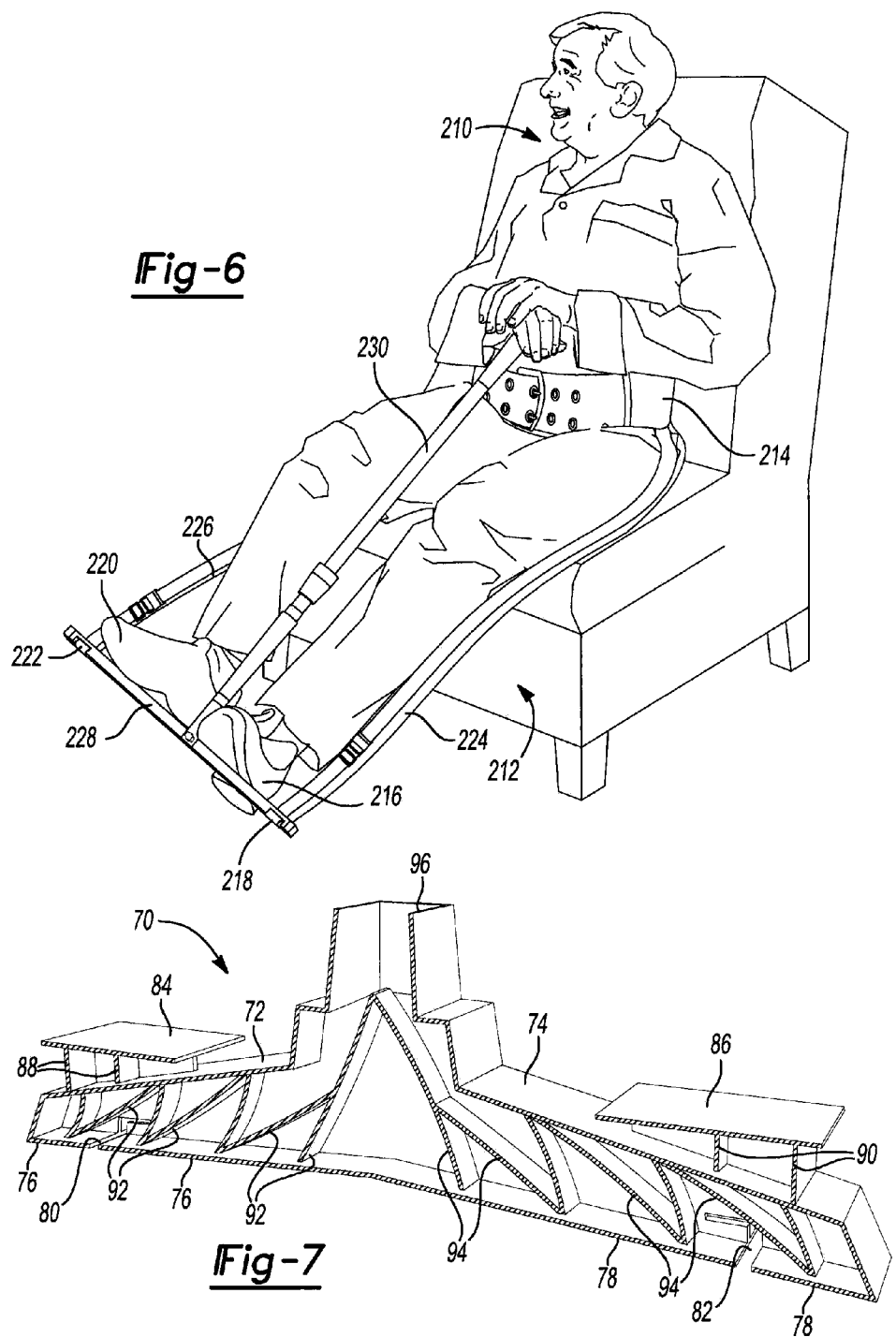

LUMBAR TRACTION DEVICE

CROSS-REFERENCE TO RELATED APPLICATIONS

This application claims the benefit of U.S. Provisional Application No. 61/260,649, filed on Nov. 12, 2009. The entire disclosure of the above application is incorporated herein by reference.

FIELD

The present disclosure relates to a lumbar traction device.

BACKGROUND

Back or lumbar pain is the second most common reason for doctor office visits in the United States after symptoms for the common cold. Furthermore, lumbar pain may severely limit the ability of the user to participate in work-related or leisurely activities. Thus, lumbar pain limits the productivity of users and excessively consumes medical resources.

Back pain is sometimes attributable to spinal stenosis, prolapsed or slipped discs and/or bulging discs. In addition to back pain, these conditions are known to also cause weakness or paralysis of muscles. Lumbar traction or distraction is a well known and effective treatment for symptoms resulting from such conditions. Most lumbar traction kits depend on gravity, hydraulics, mechanical devices and/or elastic cords. These devices, however, may be too complex for users to use or too expensive. With respect to lumbar traction kits having elastic cords, the cords store energy such that when a load is removed from the elastic cord, the energy stored in the cord is transferred back to the spine, thereby cancelling out any alleviation of symptoms.

Thus, there is a need for a simple, cheap and effective lumbar traction device. While the traction kits described herein are not a solution to all forms of back pain and disability, the disclosed lumbar traction devices can offer an inexpensive and portable relief from back pain and disability.

This section provides background information related to the present disclosure which is not necessarily prior art.

SUMMARY

In a first aspect of the disclosure a lumbar traction device is disclosed. The lumbar traction device comprises a lumbar support member to be worn adjacent to a lumbar region of a user, at least one lower leg support to be worn adjacent to a lower leg of the user; and at least one connecting member connecting the lumbar support member and the at least one lower leg support. The at least one connecting member is substantially inelastic. When a load is applied to the at least one lower leg support, the load is transferred to the lumbar support member via the at least one connecting member.

In a second aspect of the disclosure, a lumbar traction device is disclosed. The lumbar traction device comprises a lumbar support member to be worn adjacent to a lumbar region of a user, a first lower leg support to be worn adjacent to a first lower leg of the user, and a second lower leg support to be worn adjacent to a second lower leg of the user. The lumbar traction device further comprises a first connecting member connecting a first lateral section of the lumbar support member and the first lower leg support and a second connecting member connecting a second lateral section of the lumbar support member and the second lower leg support. The second lateral section of the lumbar support member is opposite to the first lateral section of the lumbar support member. When a load is applied to the first lower leg support and second lower leg support in a direction away from the lumbar traction device, the load is transferred to the lumbar support member via the first connecting member and the second connecting member.

In a third aspect of the disclosure a lumbar traction device is disclosed. The lumbar traction device comprises a lumbar support member to be worn adjacent to a lumbar region of a user, a first lower leg support to be worn adjacent to a first lower leg of the user, and a second lower leg support to be worn adjacent to a second lower leg of the user. The lumbar traction device further comprises a first connecting member connecting a first lateral section of the lumbar support member and the first lower leg support, wherein the first lower leg support is integral to the first connecting member. The lumbar traction device further includes a second connecting member connecting a second lateral section of the lumbar support member and the second lower leg support. The second lateral section of the lumbar support member is opposite to the first lateral section of the lumbar support member, and is integral to the second connecting member. The lumbar traction device further includes a foot bar interposed between the first lower leg support and the second lower leg support, wherein the foot bar removably couples to the first and second lower leg supports. When a load is applied to the foot bar, the load is transferred to the lumbar support member via the first connecting member and the second connecting member.

This section provides a general summary of the disclosure, and is not a comprehensive disclosure of its full scope or all of its features.

DRAWINGS

FIG. 6 is a drawing illustrating a user wearing an alternate embodiment of the lumbar traction device;

FIG. 7 is a drawing illustrating an alternate embodiment of the foot bar.

Figure 1:
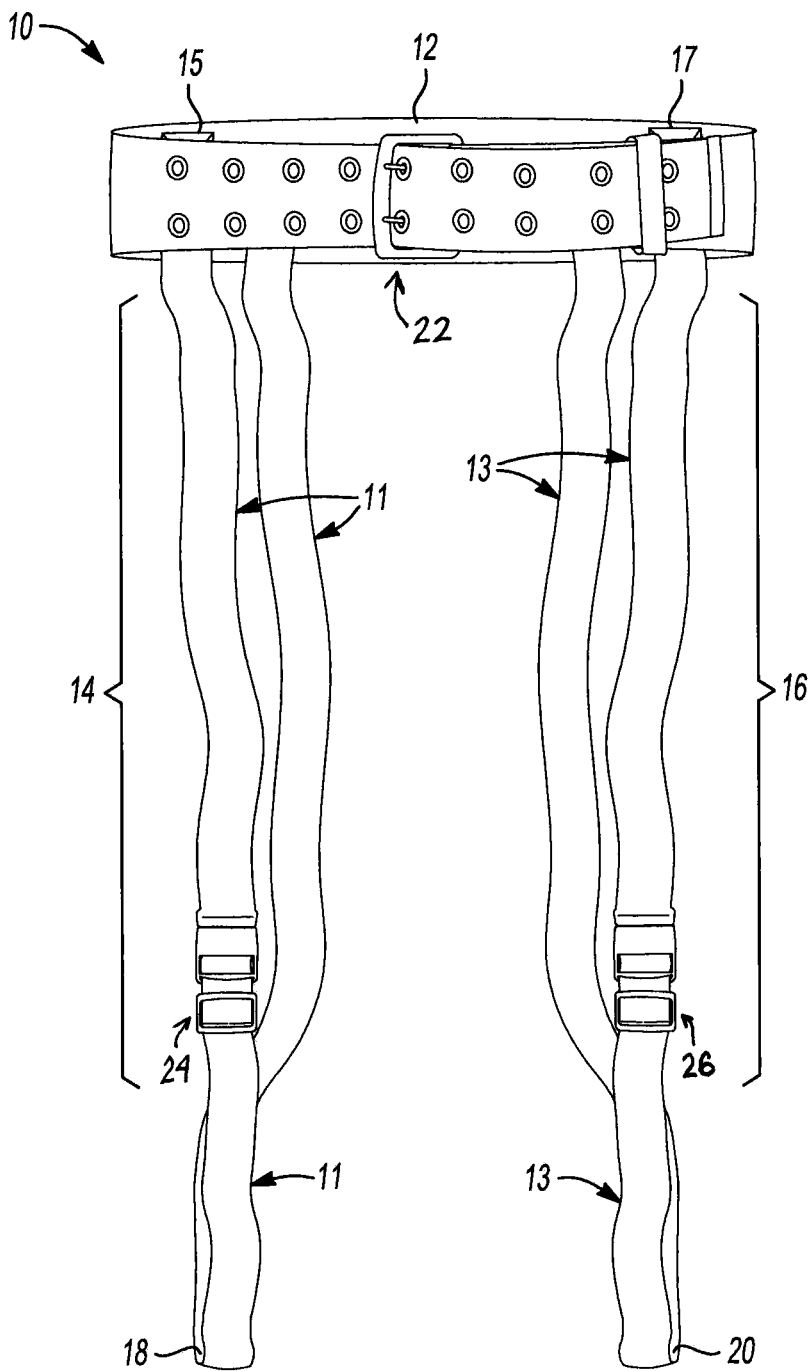
FIG. 1 is a drawing illustrating an embodiment of the lumbar traction device.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Example embodiments will now be described more fully with reference to the accompanying drawings.

FIG. 1 is a drawing illustrating an embodiment of the lumbar traction device 10. The lumbar traction device 10 can include a lumbar support member 12, which is worn adjacent to or around the back and lower abdomen resting on the pelvic (iliac) bone of the user. The lumbar traction device 10 further includes at least one lower leg support 18 and 20, and at least one connecting member 14 and 16 connecting the at least one lower leg support 18 and 20 to the lumbar support member 12.

As used herein, the lower leg can include the region of a user below the knee of the user, including at least one of the shin/calf region, the ankle, and the foot of the user.

In some embodiments, the lumbar support member 12 is a belt that can extend continuously like a ring around the back and lower abdomen and can rest on the pelvic bone, as shown in FIG. 1. The lumbar support member 12 can include a frame or ergonomic support for the lumbar region, or the lumbar support member 12 may be padded. The lumbar support member 12 can also include a fastener 22, which may include prongs, snaps, buttons, Velcro, hooks, other types of fasteners or combinations thereof. The lumbar support member 12 can be made of any flexible material that a user can wear. For instance, the belt may be composed of nylon, plastic, leather, or other materials.

In other embodiments, the lumbar support member 12 can be a frame or ergonomic support that does not fully enclose or encircle the user's waist. In these embodiments, the lumbar support member 12 can wrap or extend at least partially around the back or lower lumbar region of the user. As will be described below, when the user applies a load to the lower leg support 18 the lumbar support member 12 forcibly presses against the user's lower lumbar region.

Extending inferiorly from the lateral portions of the lumbar support member 12 are a first strap 11 and a second strap 13. The first strap 11 and second strap 13 include the first connecting member 14 and the second connecting member 16, respectively. In these embodiments, the straps 11 and 13 are U-shaped. The first strap 11 includes a first terminal end (not shown) and a second terminal end 15 attached to the anterior section and posterior section of the lumbar support member 12 respectively. The second strap 13 includes a first terminal end (not shown) and second terminal end 17 attached to anterior and posterior sections of the lumbar support member 12 respectively. The first strap 11 and second strap 13 are located at opposite ends of the lumbar support member 12. The first and second straps 11 and 13 further include the first lower leg support 18 and the second lower leg support 20, respectively. The connecting members 14 and 16 connect the lower leg supports 18 and 20 to the lumbar support member 12. The connecting members 14 and 16 are bendable, but substantially inelastic, such that when a load is applied to the lower leg supports 18 and 20, the load is transferred to the lumbar support member 12 via the connecting members 14 and 16. As used herein substantially inelastic implies that when the load is applied to the lower leg supports 18 and 20 connecting members 14 and 16, the length (L) of the connecting members 14 and 16 does not substantially change. This means that the overall length (L) of the connecting members 14 and 16 will not increase by more than 0.5%. In one embodiment the connecting members 14 and 16 and lower leg supports 18 and 20 are made of a resilient material such as a combination of polyester, nylon and polypropylene. In other embodiments, may be any other suitable substantially inelastic materials, such as lashing straps, chains, or ropes can be used, all of which can be purchased off the shelf.

In other embodiments, the straps 11 and 13 are continuous loops (not shown), and the superior ends of the loops are connected to the lateral portions of the lumbar support member 12. The connecting members 14 and 16 portion of the straps 11 and 13 may be coupled to the lumbar support member 12 in any suitable fashion. For instance, the lumbar support member 12 may include receiving members for fixedly or removeably attaching the loops thereto. Alternatively, the loops can be wrapped around the lumbar support member 12. It is envisioned that other means of connecting the loops to the lumbar support member 12 can be used as well. For instance, the superior ends of the connecting member can be sewn or stitched into the lumbar support member 12. The loops may be of fixed length or may have adjustable length so that the user can customize the length of the loops. The loops can be made adjustable by the use of rings 24 and 26, e.g., rectangular rings, or buckles. It is envisioned that other sufficient means of adjusting the rings may also be implemented.

In other embodiments, the connecting members 14 and 16 can be non-continuous and include a first terminal end that is coupled to the lumbar support member and a second terminal end that is coupled to a respective lower leg support 18 and 20. In these embodiments, the first terminal end of the connecting members 14 and 16 can be fixedly or removably attached to the corresponding lateral portion of the lumbar support member 12. For instance, the connecting members 14 and 16 may include a small continuous loop at the superior end of the strap that is sewn into or wrapped around the lumbar support member 12.

The lower leg supports 18 and 20 can be connected to or integral to the connecting members 14 and 16. In other embodiments, the lower leg supports 18 and 20 can be removably connected to the respective connecting members 14 and 16. The lower leg supports 18 and 20 are operable to receive a foot or feet of the user. The lower leg supports 18 and 20 may be the second distal end of the looped connecting member 14 and 16, as shown in FIG. 1, or may be any other structure sufficient to receive the foot, ankle, or calf region of a user. For instance, stirrups, shoes, socks, slippers, ankle bracelets, or the like may be connected to the distal end of the connecting members 14 and 16. In other embodiments, discussed further below, a foot bar may interposed between the connecting members 14 and 16.

Figure 2:
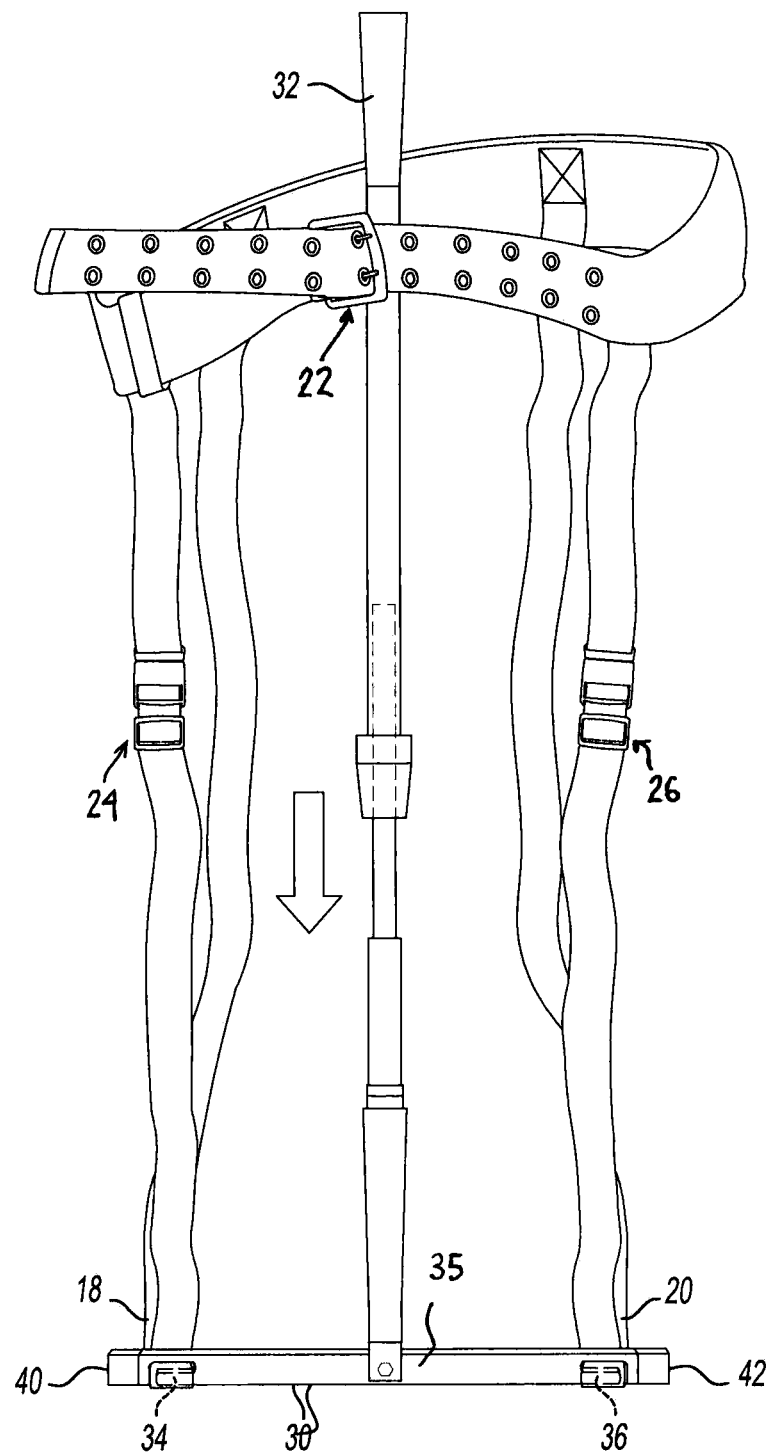
FIG. 2 is drawing illustrating an alternate embodiment of the lumbar traction device.

FIG. 2 depicts an embodiment of the lumbar traction device in which a foot bar 30 is interposed between the first lower leg support 18 and the second lower leg support 20. The foot bar 30 can be attached to the first lower leg support 18 and the second lower leg support 20 in any suitable fashion. For instance, each end 40 and 42 of the foot bar 30 may be removably coupled to the lower leg supports 18 and 20, or permanently coupled thereto. Further shown in the depicted embodiment is an optional elongated rod 32 coupled to the foot bar 30, wherein the user applies an additional downward force to the rod to increase lumbar traction. The elongated rod 32 extends upward from a middle portion 35 of the foot bar 30.

Figure 3:
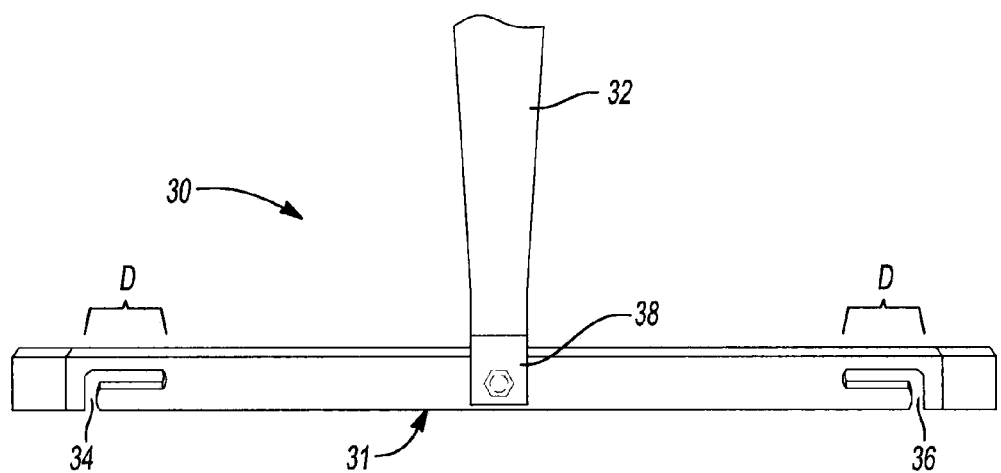
FIG. 3 is a drawing illustrating an exemplary foot bar of the lumbar traction device.

FIG. 3 depicts a front-view of an exemplary foot bar 30. The foot bar 30 includes a body 31, a first coupling portion 34 and a second coupling portion 36, for receiving the first and second lower leg supports 18 and 20, respectively. In some embodiments, the first and second coupling portions 34 and 36 are elongated slots. The foot bar 30 can further include an engaging member 38 that couples the elongated rod 32 (FIG. 2) to the middle portion 35 of the foot bar 30.

Exemplary foot bars 30 may be made of plastic, injection molded plastic, aluminum, steel, iron, or any other resilient material. The first and second coupling portions 34 and 36 are located at the lateral ends 40 and 42 of the foot bar 30. As mentioned, the first and second coupling portions 34 and 36 can be u-shaped slots. The slots have depths (D) sufficient to accommodate the respective lower leg support 18 and 20. While shown at the inferior of the foot bar 30, it is appreciated that the coupling portions 34 and 36 may be located at the superior of the foot bar 30. It is further envisioned that the coupling portions 34 and 36 can include additional components sufficient to secure the connecting means 14 and 16. In some embodiments, the coupling portions 34 and 36 may further include a securing member (not shown), such as a hinged latch, such that the lower leg support 18 or 20 is inserted in the coupling portions 34 or 36 and the spring loaded hinged latch secures the lower leg supports 18 or 20 therein. For instance, the spring loaded latch may be disposed at the opening of the coupling portions 34 or 36 of the foot bar 30, such that the lower leg support 18 or 20 is slid into the coupling portions 34 or 36 and secured by the latch, which rests at the closed position. While it is shown that the lower leg supports 18 and 20 are removably coupled to the foot bar 30, it is appreciated that in other embodiments the foot bar 30 is fixedly coupled to the lower leg supports 18 and 20.

It is appreciated that in other embodiments the lower leg supports 18 and 20 can include coupling portions sufficient to receive the foot bar 30.

Also shown in FIG. 3 is the engaging member 38. The engaging member 38 is a means for coupling the elongated rod 32 to the foot bar 30. The elongated rod 32 may be removably or fixedly coupled to the middle 35 of the foot bar 30. The engaging member 38 can be any structure sufficient to secure the elongate rod 32 to the body 31 of the foot bar 30. For instance, the engaging member 38 may be a receptacle that receives the elongated member. The receptacle can have depth sufficient to engage the elongated member. For instance, the receptacle may have a depth of 2-4 inches. It is appreciated that the depth, however, may be greater or less than the provided depth range. It is further noted that other engaging members 38 can be used. For example, the elongated rod 32 can have a threaded receptacle at the central axis of the distal end of the elongated rod 32 for receiving an engaging member 38, e.g. a screw. Alternatively, the foot bar 30 can include a threaded receptacle, such that a screw extending out of the central axis of the distal end of the elongated rod 32 screws into the threaded receptacle. It is envisioned that other means for securing the elongated rod 32 to the foot bar 30 are also sufficient. For instance, the elongated rod 32 may be permanently fixed to the foot bar.

Referring back to FIG. 2, the elongated rod 32 has length sufficient to extend from the foot bar 30 to within the reach of the user. The elongated rod 32 can extend superiorly from a central area of the body 31 of the foot bar 30. The elongated rod 32 can be substantially perpendicular to the lateral axis of the foot bar 30. In some embodiments, the elongated rod 32 may be telescoping, such that the length can be selectively increased or decreased. Further, in some embodiments, the elongated rod 32 may have a handle at an end proximate to the user. The user can use the elongated rod 32 to increase the load that is applied to the foot bar 30 by forcibly pressing downward on the elongated rod 32 towards the foot bar 30, such that the load is transferred from the elongated rod 32 to the foot bar 30, and to the lumbar support member 12 via the connecting members 14 and 16.

As described, in some embodiments the foot bar 30 is interposed between the first and second connecting members 14 and 16 such that the connecting members 14 and 16 may be removably coupled to the foot bar 30. In these embodiments, the user may place one or both feet on the foot bar and apply a downward force to the foot bar 30. The foot bar 30 transfers the load to the lumbar support member 12 via the connecting members 14 and 16. Alternatively, the user can remove the foot bar 30 and place his feet at the lower leg supports 18 and 20 at the distal ends of the connecting members 14 and 16. As discussed, the foot bar 30 may be removably coupled to the first and second lower leg support 18 and 20. The foot bar 30 can be removed, such that the lumbar traction device is similar to the embodiments discussed with respect to FIG. 1.

Figure 4:
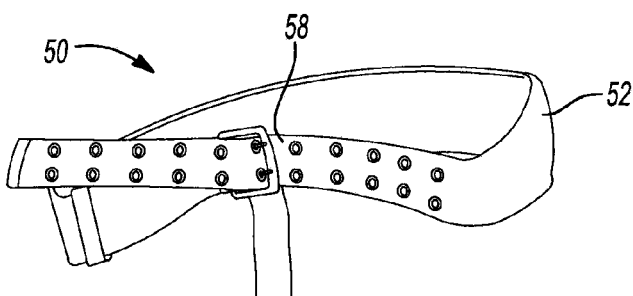
FIG. 4 is a drawing illustrating an alternate embodiment of the exemplary lumbar traction device.
Figure 4:
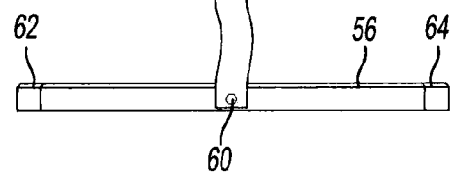

FIG. 4 illustrates an alternative embodiment of the lumbar traction device 50. In these embodiments, the lumbar traction device 50 is comprised of a lumbar support member 52, a foot bar 56, and a connecting member 54 connecting an anterior section 58 of the lumbar support member 52 and the foot bar 56. A fastener 60 attaches the connecting member 54 to the foot bar 56. It is envisioned that alternative means for affixing the foot bar 56 to the connecting means can be implemented as well. The connecting member 54 can be affixed to the lumbar support member 52 in the manner described above, with respect to FIGS. 1 and 2. For instance, the connecting member 54 can be stitched into the anterior section 58 of the lumbar support member or may loop around the anterior section 58 of the lumbar support member. It is envisioned that additional supports (not shown) may connect the distal ends 62 and 64 of the foot bar 56 to the connecting member 54.

A user can use the lumbar traction device 50 by wearing the lumbar support member 52 around his or her waist. The user places his or her feet at the distal ends 62 and 64 of the foot bar 56 and applying a downward force onto the foot bar 56. The downward force is transferred to the lumbar support member 52 via the connecting member 54.

It is appreciated that the lumbar support member 52 and the connecting member 54 can be substantially similar to the lumbar support member 12 and connect members 14 and 16 described above. The foot bar 56 can also be substantially similar to the foot bar 30, described above. The foot bar 56 may further include a fastener 60 for connecting the connecting member 54 to the foot bar 56. Alternatively, the fastener 60 can be a hook or clip which receives the connecting member 54. It is envisioned that other connecting means sufficient to couple the fastener 60 to the foot bar 56 are also within the scope of the disclosure.

Figure 5:
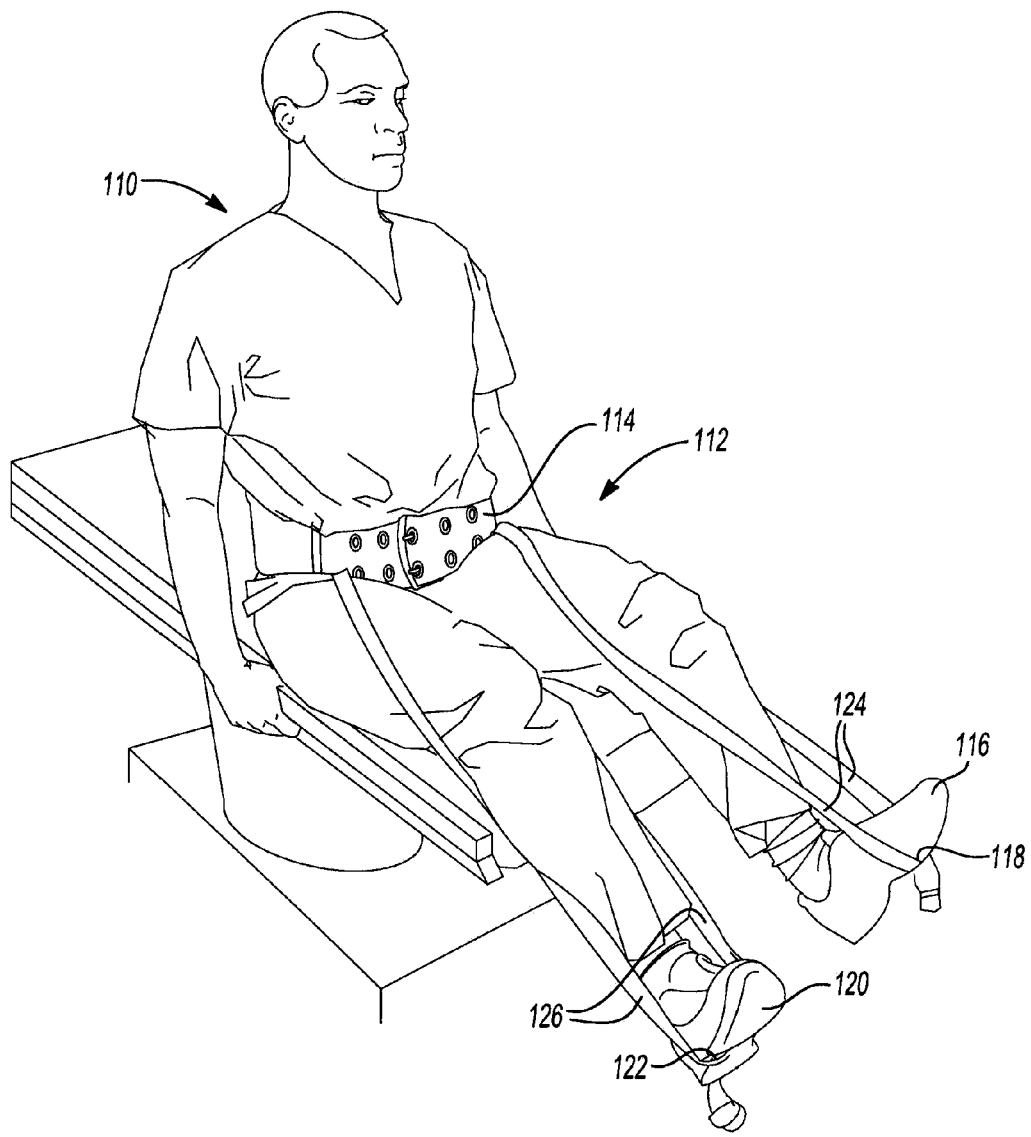
FIG. 5 is a drawing illustrating a user wearing an embodiment of the lumbar traction device.

FIG. 5 illustrates an embodiment of lumbar traction device 112 in use by a user 110. As can be seen, the user 110 is wearing the lumbar support member 114 around his waist. The user places his left foot 116 in a first lower leg support 118 and his right foot 120 in a second lower leg support 122. A first connecting member 124 connects the first lower leg support 118 to the lumbar support member 114 and a second connecting member 126 connects the second lower leg support 122 to the lumbar support member 114. The user 110 exerts a downward force on the lower leg supports 122 and 118. While recumbent, a pillow may be placed under the legs for support. By extending the hips and knees and plantar flexing of the feet at the first and second lower leg support 118 and 122, a load is transferred to the lumbar support member 114, which forcibly presses against the lower lumbar region of the user. As this occurs the hip bone (pelvis) to which the sacrum is attached is distracted from the lumbar vertebrae i.e. pushed towards the feet, relieving the pressure on the nerves in the lower back. As described, the connecting members 124 and 126 are substantially inelastic, thus when the user removes the downward force from the lower leg supports 122 and 118, no recoil is felt at the lumbar support member and the pelvis remains distracted from the vertebrae.

FIG. 6 illustrates an alternative embodiment of the lumbar traction device 212 in use by a user 210. As can be seen, the user 210 is wearing the lumbar support member 214 around his waist. The lumbar traction device 212 includes a foot bar 228, which connects the first lower leg support 218 and the second lower leg support 222. The user places his left foot 216 and right foot 220 on the foot bar 228 and applies a downward force to the foot bar 228 by flexing his knees and hips and flexing his feet 220 and 216. This will cause the force to be transferred to the lumbar support member 214, which causes the pelvis to be distracted from the lumbar vertebrae. Furthermore, the user 210 can apply a downward force to the foot bar 228 by pushing down axially on the elongate rod 230. The downward force applied to the foot bar 228 via the elongate rod 230 can be in addition to or in lieu of the downward force applied to the foot bar 228 via the user's feet 216 and 220.

As previously discussed, the connecting members 224 and 226 are substantially inelastic. Thus, there is very little energy stored in the connecting members 224 and 226 when the user exerts the downward force on the foot bar 228. Accordingly, when the patient removes the downward force applied to the foot bar 228, no recoil is felt at the lumbar support member, thereby allowing the pelvis to remain distracted from the vertebrae.

FIG. 7 illustrates a cross-sectional view of an alternative embodiment of a foot bar 70. The exemplary foot bar 70 includes a first superior extension 72, a second superior extension 74, a first inferior extension 76, and a second inferior extension 78. The first and second superior extensions 72 and 74 slope downward as the superior extension 72 and 74 extend from the center of the foot bar 70. The first and second inferior extensions 76 and 78 are less sloped and extend from the center of the foot bar 70. It is appreciated that the inferior extensions 76 and 78 may have a slight upward or downward slope. Connecting the first superior extension 72 and the first inferior extension 76 are connected by a first plurality of ribs 92. In the exemplary embodiment, the ribs 92 are slanted, but it is appreciated that the ribs may also be substantially vertical as well. Similarly, the second superior extension 74 and the second inferior extension 76 are connected by a second plurality of ribs 94.

The foot bar 70 also includes a first coupling portion 80 and second coupling portion 82 for receiving the first and second connecting members 14 and 16, respectively. A coupling portions 80 or 82 can be a slot with sufficient depth to receive the respective connecting member. While shown as being located at the distal end of the inferior extensions 76 and 78, it is appreciated that the coupling portions 80 and 82 may be alternatively located at the superior extensions as well.

The exemplary foot bar 70 can also include a first foot rest 84 and a second foot rest 86, wherein the foot rests 84 and 86 are raised from the body of the foot bar 70. The first foot rest 84 can be supported by a third plurality of ribs 88, which extend in a substantially vertical manner from the first superior extension 82. Similarly, the second foot rest 86 can be supported by a fourth plurality of ribs 90, which extend in a substantially vertical manner from the second superior extension 84 ribs. The exemplary foot bar 70 can further include an engaging member 96 configured to receive the elongate rod. The engaging member 96 can be a rectangular opening with sufficient depth to receive the elongate rod. It is envisioned that in alternative embodiments, the engaging member 96 can also be a screw, which the elongate rod can screw onto, or other sufficient means to connect the elongate rod to the foot bar 70.

The exemplary foot bars 70 can be composed of plastic, injection molded plastic, aluminum, steel, iron, or any other resilient material.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A lumbar traction device comprising: a lumbar support member configured to be worn adjacent to a lumbar region of a user;
   a first lower leg support and a second lower leg support configured to be worn adjacent to a respective first and second lower leg of the user; and
   a first connecting member and a second connecting member each having a proximate end connected to the lumbar support member and a distal end connected to the first and second lower leg support, respectively, the first and second connecting members being substantially inelastic such that a length of the first and second connecting members measured from the proximate ends and distal ends are substantially fixed,
   a foot bar interposed between the first lower leg support and the second lower leg support, wherein the foot bar removably couples to the first and second lower leg supports, and wherein the first lower leg support is coupled to the first connecting member and the second lower leg support is coupled to the second connecting member; and
   an elongated rod coupled to the foot bar, wherein the elongated rod is configured to receive a downward force from the user to increase the load transferred to the lumbar support member.

2. The lumbar traction device of claim 1 wherein the foot bar includes a first superior surface, a second superior surface, a first inferior surface and a second inferior surface, wherein a distal end of the first superior surface slopes downward towards a distal end the first inferior surface, and a distal end of the second superior surface slopes downward towards a distal end of the second inferior surface.

3. The lumbar traction device of claim 2 wherein a first plurality of ribs extend from the first superior surface to the first inferior surface and a second plurality of ribs extend from the second superior surface to the second inferior surface.

4. The lumbar traction device of claim 1 wherein the first and second connecting members are connected to an anterior section of the lumbar support member.

5. The lumbar traction device of claim 1 wherein the length of the at least one connecting member is limited to increase only within 0.5% when the load is applied to the first and second lower leg supports.

6. A lumbar traction device comprising:
   a lumbar support member configured to be worn adjacent to a lumbar region of a user;
   a first lower leg support configured to be worn adjacent to a first lower leg of the user;
   a second lower leg support configured to be worn adjacent to a second lower leg of the user;
   a first connecting member connecting a first lateral section of the lumbar support member and the first lower leg support, the first connecting member being substantially inelastic;
   a second connecting member connecting a second lateral section of the lumbar support member and the second lower leg support, wherein the second lateral section of the lumbar support member is opposite to the first lateral section of the lumbar support member, the second connecting member being substantially inelastic;
   a foot bar interposed between the first lower leg support and the second lower leg support; and
   an elongated rod coupled to the foot bar;
   wherein a load applied to the foot bar from the elongated rod in a direction away from the lumbar support member is transferred to the lumbar support member via the first connecting member and the second connecting member.

7. The lumbar traction device of claim 6 wherein the foot bar includes a first superior surface, a second superior surface, a first inferior surface and a second inferior surface, wherein a distal end of the first superior surface slopes downward towards a distal end of the first inferior surface, and a distal end of the second superior surface slopes downward towards a distal end of the second inferior surface.

8. The lumbar traction device of claim 7 wherein a first plurality of ribs extend from the first superior surface of the foot bar to the first inferior surface of the foot bar and a second plurality of ribs extend from the second superior surface of the foot bar to the second inferior surface of the foot bar.

9. The lumbar traction device of claim 6 wherein the foot bar removably couples to the first and second lower leg supports.

10. The lumbar traction device of claim 6 wherein the first lower leg support is integral to the first connecting member and the second lower leg support is integral to the second connecting member.

11. A lumbar traction device comprising:
  a lumbar support member configured to be worn adjacent to a lumbar region of a user;
  a first lower leg support configured to be worn adjacent to a first lower leg of the user;
  a second lower leg support configured to be worn adjacent to a second lower leg of the user;
  a first connecting member connecting a first lateral section of the lumbar support member and the first lower leg support, the first connecting member being substantially inelastic, and wherein the first lower leg support is integral to the first connecting member;
  a second connecting member connecting a second lateral section of the lumbar support member and the second lower leg support, wherein the second lateral section of the lumbar support member is opposite to the first lateral section of the lumbar support member, the second connecting member being substantially inelastic, and wherein the second lower leg support is integral to the second connecting member;
  a foot bar interposed between the first lower leg support and the second lower leg support, wherein the foot bar removably couples to the first and second lower leg supports; and
  an elongated rod coupled to the foot bar, wherein the elongated rod is substantially perpendicular to the foot bar, and wherein the rod is configured to increase the load transferred to the lumbar support member resulting from a force applied to the rod;
  wherein a load applied to the foot bar from the elongated rod is transferred to the lumbar support member via the first connecting member and the second connecting member.

* * * * *